United States Patent [19]

Eibl et al.

[11] Patent Number: 5,580,962
[45] Date of Patent: Dec. 3, 1996

[54] PARENTERALLY ADMINISTRABLE DRUG HAVING THROMBOLYTIC ACTIVITY AND CONTAINING PROTEIN C

[75] Inventors: Johann Eibl; Yendra Linnau, both of Vienna; Anton Philapitsch, Ebenfurt; Hans P. Schwarz, Vienna, all of Austria

[73] Assignee: Immuno Aktiengesellschaft, Vienna, Austria

[21] Appl. No.: 416,533

[22] Filed: Apr. 3, 1995

Related U.S. Application Data

[63] Continuation of Ser. No. 905,541, Jun. 18, 1992, abandoned.

[30] Foreign Application Priority Data

Jun. 20, 1991 [AT] Austria ................................. 1239/91

[51] Int. Cl.⁶ ........................... C07K 3/00; A61K 38/43; A61K 38/48
[52] U.S. Cl. .................... 530/395; 424/94.1; 424/94.63; 424/94.64
[58] Field of Search ................ 424/94.1, 94.2, 424/94.63, 94.64; 530/395

[56] References Cited

U.S. PATENT DOCUMENTS

| | | | |
|---|---|---|---|
| 5,084,274 | 1/1992 | Griffin et al. | 424/94.64 |
| 5,316,766 | 5/1994 | Baldus et al. | 424/94.63 |
| 5,350,578 | 9/1994 | Griffin et al. | 424/94.64 |
| 5,372,812 | 12/1994 | Reed et al. | 424/145.1 |
| 5,407,673 | 4/1995 | Reich et al. | 424/94.64 |
| 5,453,373 | 9/1995 | Gerlitz et al. | 435/240.2 |
| 5,478,558 | 12/1995 | Eibl et al. | 424/94.63 |

FOREIGN PATENT DOCUMENTS

| | | |
|---|---|---|
| 39961/89 | 2/1990 | Australia . |
| 30329/89 | 8/1992 | Australia . |
| 0050061 | 9/1981 | European Pat. Off. . |
| 0131740 | 6/1984 | European Pat. Off. . |
| 0159311 | 2/1985 | European Pat. Off. . |
| 0287028 | 4/1988 | European Pat. Off. . |
| 0318201 | 11/1988 | European Pat. Off. . |
| 90/12028 | 7/1990 | WIPO . |
| 90/07524 | 7/1990 | WIPO . |

OTHER PUBLICATIONS

"Advances in Applied Biotechnology Series", vol. 11, "Protein C and Related Anticoagulants" (Bruley and Drohan eds.), Gulf Publishing Co., Houston, London, Paris, Tokyo (1990), pp. 83–89.

O. Taby, J. Chabbat and M. Steinbuch, "Inhibition of Activated Protein C by Aprotinin and the Use of the Insolubilized Inhibitor for its Purification"; Thrombosis Research 59: 27–35, 1990.

G. Koehler, C. Milstein, "Continuous cultures of fused cells secreting antibody of predefined specificity"; Nature vol. 256, (1975), pp. 495–497.

Esmon, C. T. et al., "TCM," vol. 5(4), pp. 141–148.

Hirahara, K. et al., "Chem. Pharm. Bull.," vol. 37, #3, pp. 692–696, 1989.

Primary Examiner—Michael G. Wityshyn
Assistant Examiner—Kristin Larson
Attorney, Agent, or Firm—Foley & Lardner

[57] ABSTRACT

A thrombolytic, parenterally administrable drug containing activated protein C is provided for. The drug is free of serum amyloid P, thrombin activity, infectious agents and antibodies against protein C and activated protein C.

2 Claims, 1 Drawing Sheet

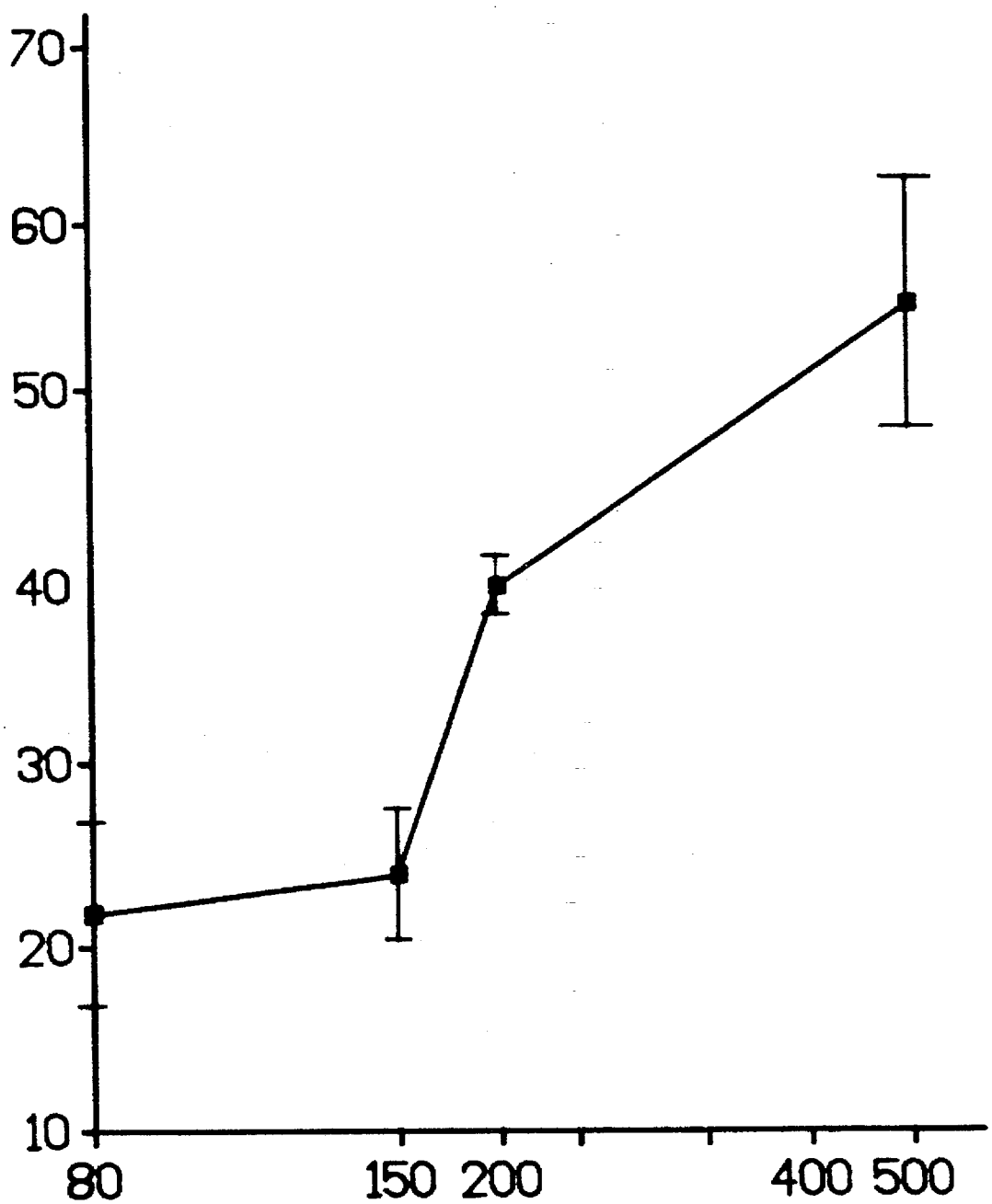

PARENTERALLY ADMINISTRABLE DRUG HAVING THROMBOLYTIC ACTIVITY AND CONTAINING PROTEIN C

This application is a continuation of application Ser. No. 07/905,541, filed Jun. 18, 1992, now abandoned.

BACKGROUND OF THE INVENTION

The invention relates to a parenterally administrable drug having thrombolytic activity and containing activated protein C free of thrombin activity and of antibodies directed against protein C or activated protein C.

These drugs may be applied as thrombolytic agents, as fibrinolytic agents and as anticoagulants as well as in the treatment of protein C-deficiencies.

Protein C is a vitamin K-dependent glycoprotein that is synthesized in the liver and circulates in plasma as an inactive zymogen at a concentration of 4 µg/ml. It is converted into the active serine protease (activated protein C) by the thrombin-thrombomodulin complex on the surface of the vessel wall (endothelium). It is known that activated protein C has profibrinolytic properties. It also has an anticoagulant effect, because it proteolytically degrades both factor Va, the cofactor for the factor Xa-induced prothrombin activation (thrombin formation), and factor VIIIa, the cofactor for the factor IXa-induced factor X activation.

The activation of protein C in vivo constitutes a negative feedback reaction in the generation of thrombin. In order to develop the optimum biologic activity, a co-factor (protein S) is necessary.

In the PCT Publication WO 90/12028 as well as in EP-A - 0 287 028, methods of activating protein C and affinity chromatographic purification are described. According to EP-A - 0 287 028, the reaction of protein C with thrombin/thrombomodulin is stopped by the addition of antithrombin III.

When administering protein C preparations purified on non-sterile monoclonal antibodies by way of affinity chromatography, there is the danger of transmitting pathogens. In addition, impurities, such as traces of thrombin, traces of murine proteins or serum amyloid P may have adverse effects in the administration of preparations that contain activated protein C.

To increase the virus safety of protein C preparations it is suggested in "Advances in Applied Biotechnology Series", Vol. 11, "Protein C and Related Anticoagulants" (Bruley D. F. and Drohan W. N. eds), Gulf Publishing Company, Houston, London, Paris, Zurich, Tokyo, pp. 83–89 (1990), to isolate protein C from a previously virus inactivated starting material by affinity chromatographic purification on virus inactivated monoclonal antibodies. Subsequently, the preparation may be subjected to a further treatment for virus inactivation.

From PCT Publication WO 90/07524 it is known that serum amyloid P can be eliminated by adsorption of protein C on an ion exchanger (SEPHADEX Q50).

Furthermore, activated protein C can be freed from traces of thrombin by the selective adsorption of the thrombin on heparin-SEPHAROSE (Thromb. Res. 59, 27–35 (1990)). However, that method does not comprise any step for virus inactivation or for the removal of serum amyloid P.

In EP-A - 0 318 201 it is stated that activated protein C alone or in combination with a thrombolytically active substance may be used to prevent arterial thromboses or thromboembolic conditions. The antithrombotic activity of activated protein C is demonstrated by examples.

SUMMARY OF THE INVENTION

It is an object of the invention to provide a drug having thrombolytic activity, which contains activated protein C of a particularly high purity and is free of thrombin activity and antibodies directed against protein C or activated protein C.

The drug according to the invention is characterized in that it is free of serum amyloid P and of infectious agents.

The drug according to the invention does not cause any side reactions upon administration: thrombolysis therapy does not induce a drop of fibrinogen or bleedings.

It has been shown that the drug according to the invention, in particular, in combination with Lys-plasminogen or urokinase, has a surprisingly good thrombolytic activity, thus being capable of largely preventing thromboses.

BRIEF DESCRIPTION OF THE FIGURE

The figure depicts data obtained from rabbits infused with various doses of activated protein C.

DETAILED DESCRIPTION OF PREFERRED EMBODIMENTS

The invention is based on the finding that the administration of activated protein C involves the liberation of the thrombolytically active enzyme plasmin in the organism, thus increasing the thrombolytic activity in vivo. Therefore, the drug according to the invention is suitable for use as a thrombolytic agent. It has, furthermore, been shown that the thrombolytic activity is a function of the dose applied, and exhibits optimum thrombolytic activity if the activated protein C used is free of thrombin activity and of serum amyloid P.

The invention also relates to a method of obtaining the above-described drug, which method is characterized by a combination of the following measures:

purifying protein C by way of affinity chromatography with anti-protein C antibodies optionally inactivated against infectious agents, activating the purified protein C with thrombin and subsequently inhibiting the thrombin, freeing the activated protein C from serum amyloid P and from antibodies chromatographically by aid of ion exchangers, and processing to a parenterally administrable drug.

A preferred embodiment of the method according to the invention is characterized in that at least two measures are taken to inactivate infectious agents.

The drug according to the invention contains activated protein C in a particularly pure form. It is best to inhibit and subsequently remove thrombin from the reaction mixture by means of 0.01 to 0.1 IU antithrombin III per unit of thrombin in the form of an antithrombin III-heparin complex. The antithrombin III-heparin complex has a considerably higher affinity to thrombin than antithrombin III alone, for which reason the separation of thrombin from activated protein C is more readily feasible.

In addition to being free of traces of thrombin, the drug according to the invention also is free of murine proteins (antibodies) and serum amyloid P by way of chromatographic purification on an ion exchanger and, in addition, may be regarded as virus safe on account of severally combined treatments for virus inactivation. To obtain the zymogen, previously virus inactivated starting material (prothrombin complex) may be purified by way of affinity chromatography on virus-inactivated monoclonal antibodies. After activation with thrombin, the activated protein C again may be subjected to a treatment for virus inactivation. Known inactivation methods (e.g., EP-A - 0 159 311, EP-A - 0 050 061. EP-A - 0 131 740) may be used to inactivate human pathogenic germs.

Advantageously, the inhibition of thrombin is effected by the addition of antithrombin III-heparin complex.

In the following, the preparation of a pharmaceutical composition containing activated protein C and its thrombolytic activity as observed in an animal model will be described in detail.

Preparation of Protein C

Pure protein C was recovered from a crude protein C fraction obtained from commercially available prothrombin complex concentrate. Purification was effected by affinity chromatography by means of monoclonal antibodies. Monoclonal anti-protein C anti-bodies were produced as follows:

BALB/C mice were immunized with 100 µg human protein C by intraperitoneal injection at two-week intervals. After six weeks, another 50 µg of human protein C were injected and fusion was carried out three days later. The myeloma cell line (P3-X-63-AG8-653, $1.5 \times 10^7$ cells) was mixed with $1.7 \times 10^8$ mouse spleen cells and fused according to the modified method of Köhler & Milestein by using PEG 1500 (Köhler G., Milestein C., Nature 256 (1975), 495–497).

Positive clones, assayed by means of enzyme linked immunosorbant assay ("ELISA"), were subcloned twice. Ascites production was effected by injection of $5 \times 10^6$ hybridoma cells per BALB/C mouse two weeks after Pristan treatment.

The immunoglobulin was purified from ascites by means of ammonium sulfate precipitation and subsequent chromatography on QAE-SEPHADEX and, further, by chromatography on SEPHADEX G200. To reduce the risk of transmission of murine viruses, the antibody was subjected to a further virus inactivation step prior to immobilization. The monoclonal protein C antibodies thus obtained were coupled to CNBr-activated SEPHAROSE 4B (Pharmacia). The following buffers were used for the purification of protein C by means of affinity chromatography:

Adsorption buffer: 20 mM Tris, 2 mM EDTA, 0.25M NaCl and 5 mM benzamidine;

Washing buffer: 20 mM Tris, 1M NaCl, 2 mM benzamidine, 2 mM EDTA, pH 7.4;

Elution buffer: 3M NaSCN, 20 mM Tris, 1M NaCl, 0.5 mM benzamidine, 2 mM EDTA.

In detail: The prothrombin complex concentrate was dissolved in the adsorption buffer, with approximately 10 g of the prothrombin complex concentrate being employed for a 20 ml monoclonal antibody column. Subsequently, the dissolved prothrombin complex concentrate was filtered, centrifuged at 20,000 r.p.m. for 15 min and sterilely filtered through a 0.8 µm filter. The sterilely filtered and dissolved prothrombin complex concentrate was applied to the column at a flow rate of 10 ml/h. Subsequently, the column was washed free of protein with the washing buffer, and finally the bound protein C was eluted by means of the elution buffer at a flow rate of 5 ml/h and the fractions were collected. The eluted protein C was dialyzed against a buffer (0.2 mol/l Tris, 0.15M glycine and 1 mM EDTA, pH 8.3). Protein C antigen concentration was determined using the immunoelectrophoresis method described by Laurell, *Analyt. Biochem.* 15: 45–52 (1966), and protein C activity was determined using PROTAC activation.

The protein C-containing solution obtained was sterilely filtered, lyophilized and virus inactivated by one-hour vapor treatment at 80° C.±5° C. and 1375±35 mbar.

Preparation of Activated Protein C

The activation of purified protein C was effected in that 10 g protein C was dissolved in a buffer (150 mM NaCl, 15 mM sodium citrate, pH=7.5) at a concentration of 6 mg/ml and incubated for three hours at 37° C. with 14.4 mg human virus inactivated thrombin dissolved in 100 mM NaCl and 10 mM sodium citrate buffer. The reaction was stopped with 1,200 U antithrombin III-heparin complex.

After this, further purification of the activated protein C was performed on Q-SEPHAROSE. To this end, adsorption was carried out in 150 mM NaCl and 15 mM sodium citrate; elution was performed with 1M NaCl solution.

The eluate was ultrafiltered, sterilely filtered, sterilely filled at units of 5 ml each and lyophilized.

Upon dissolution to a volume of 5 ml, the preparation had the following composition:

Protein: 1.5 mg/ml aPC: 204 U/ml (amidolytically with chromogenic substrate S2366 by Kabi)

NaCl: 150 mM

Sodium citrate: 15 mM pH: 7.5

The preparation was free of antibodies against protein C and thrombin (immunologically determined) and, in addition, was free of serum amyloid P (electrophoretically determined).

Animal Model

The thrombolytic property of human activated protein C was evaluated in a model known in the literature and considered as a standard for testing thrombolytic substances. The model described by D. Collen in 1983 was modified by using $^{123}$human fibrinogen instead of $^{125}$I fibrinogen and employing a gamma camera (by Elscint APEX 409AG, Single Pinhole Collimator).

The left jugular vein of HYPNORM (Janssen) anesthesized rabbits was exposed and a catheter was bound into the ramus facialis. After clamping of the jugular vein over a distance of about 1.5 cm, 100 µl of a $^{123}$I fibrinogen-rabbit blood mixture was applied through the catheter. After 30 minutes the clamps were removed. aPC was infused through the femoral vein for 1 hour. The gamma camera was placed over the $^{123}$I fibrinogen thrombus at a distance of 2 cm. The radioactivity was measured for 2 hours and continuously recorded. The values were corrected by the decay of the $^{123}$I fibrinogen. The rate of thrombolysis was expressed as the drop of radioactivity in the thrombus.

Four animals were used for each dose lot. One lot was pretreated with coumarin (4-hydroxycoumarin, Sigma, 5 mg/kg i.v. for 9 days) in order to eliminate the synthesis of vitamin-K-dependent coagulation factors. The thrombi in the anticoagulated animals were produced by aid of a normal, i.e., non-anticoagulated, rabbit blood-fibrinogen mixture.

Infusion of aPC caused a dose-dependent thrombolysis: 80, 150, 200 and 500 U/kg induced 21, 24, 40 and 58% thrombolysis, respectively. Buffer-treated animals merely showed 12% lysis during the same measuring period of 2 hours. The anticoagulated animals were lysis-resistant, exhibiting no more than 18% lysis at 400 U/kg. This demonstrates that vitamin-K-dependent proteins (e.g., protein S, protein Z, prothrombin) are necessary for the thrombolytic effect of aPC in vivo.

These results are illustrated graphically in the figure, the abscissa indicating the dose (units/kg) and the ordinate indicating the thrombolytic effect (% lysis).

It was demonstrated that aPC is more suitable for the dissolution of venous thrombi than a combination of aPC with t-PA. When administering 500 units aPC/kg and 0.4 mg t-PA/kg, a lysis of only about 33% could be observed (as compared to 58% when applying aPC alone).

What We claim is:

1. A method of producing a pharmaceutical preparation for thrombolysis comprising activated protein C, consisting essentially of the steps of:

(a) purifying protein C with anti-protein C antibodies to obtain a purified protein C preparation;

(b) contacting said purified protein C preparation with thrombin to obtain an activated protein C preparation;

(c) inhibiting said thrombin by contact with an inhibitor to obtain an activated protein C preparation that is free of thrombin activity and contains a thrombin-inhibitor complex;

(d) purifying the activated protein C preparation of step (c) by ion exchange chromatography to remove serum amyloid P, antibodies and the thrombin-inhibitor complex from said preparation; (e) inactivating viruses present in the purified activated protein C preparation; and (f) recovering said purified activated protein C preparation to form said pharmaceutical preparation for thrombolysis.

2. A method according to claim 1, wherein in step (c) said inhibitor is an antithrombin III-heparin complex.

* * * * *